(12) United States Patent
Perring et al.

(10) Patent No.: US 6,475,473 B1
(45) Date of Patent: Nov. 5, 2002

(54) PERFUME COMPOSITIONS

(75) Inventors: Keith D. Perring, Kent (GB); Philip W. Goulding, Kent (GB); John M. Behan, Kent (GB)

(73) Assignee: Quest International B.V., Naarden (NL)

( * ) Notice: Subject to any disclaimer, the term of this patent is extended or adjusted under 35 U.S.C. 154(b) by 0 days.

(21) Appl. No.: 09/743,140

(22) PCT Filed: Jul. 6, 1999

(86) PCT No.: PCT/GB99/02163

§ 371 (c)(1),
(2), (4) Date: Jan. 5, 2001

(87) PCT Pub. No.: WO00/01360

PCT Pub. Date: Jan. 13, 2000

(30) Foreign Application Priority Data

Jul. 7, 1998 (GB) ................................................ 9814650

(51) Int. Cl.⁷ ............................ A61K 7/32; A61K 7/06; A61K 9/14; A61K 7/075; A61K 7/46
(52) U.S. Cl. ........................ 424/65; 424/70.1; 424/400; 424/401; 424/489; 510/119; 510/130; 510/276; 512/1; 512/8; 512/20; 512/25; 512/26; 512/27
(58) Field of Search ................................. 424/400, 401, 424/65, 70.1, 489; 510/119, 130, 276; 512/1, 8, 20, 25, 26, 27

(56) References Cited

U.S. PATENT DOCUMENTS

| 3,325,369 A | | 6/1967 | Sommerville |
| 5,733,535 A | | 3/1998 | Hollingshead et al. |
| 5,780,404 A | * | 7/1998 | Bacon et al. ................ 510/101 |
| 6,086,903 A | * | 7/2000 | Trinh et al. .................. 424/401 |

FOREIGN PATENT DOCUMENTS

| EP | 076 493 | | 4/1983 |
| EP | 545 556 | | 6/1993 |
| EP | 0834 551 | | 4/1998 |
| FR | 2 666 510 | | 3/1992 |
| WO | WO 97/30689 | | 8/1997 |
| WO | WO 98/20101 A1 | * | 5/1998 |

* cited by examiner

Primary Examiner—José G. Dees
Assistant Examiner—Marina Lamm
(74) Attorney, Agent, or Firm—Morgan, Lewis & Bockius LLP

(57) ABSTRACT

A perfume composition contains at least 15% by weight one or more defined aldehydes, and at least 30% by weight of at least one of five defined categories of hydroxylic materials, ketones, ethers, esters and nitriles. The perfume composition exhibits a deodorant effect, is particularly good at reducing sulphurous malodors, and is suitable for use in deodorant products, personal products and laundry treatment products.

14 Claims, No Drawings

PERFUME COMPOSITIONS

This invention relates to perfume compositions, that is to say compositions of fragrance materials, to personal products and other products containing such perfume compositions, and to the use of such perfume compositions to give a deodorant effect.

EP-B-3172, EP-A-5618, U.S. Pat. Nos. 4,304,679, 4,322,308, 4,278,658, 4,134,838, 4,288,341, 4,289,641 and 4,906,454 all describe perfume compositions which exhibit a deodorant action, (i.e. addresses the problem of human body odour, particularly that of the axillae) either when applied to human skin using a cosmetically acceptable vehicle or when included in a detergent product or fabric conditioning product used in laundering of textiles. EP-B-147191 and U.S. Pat. No. 4,663,068 describes deodorant perfume compositions which are stable in the presence of bleaching materials.

A difficulty with the perfume compositions disclosed in these documents is that they generally include appreciable quantities of relatively high molecular weight perfume components which help to extend the effective lifetime of deodorant action following product application, but which tend to have less perfume impact and to exhibit odour characteristics which span a finite range. This limitation on perfume composition represents a compromise between long term deodorant efficacy and optimal hedonic performance.

We have now found that deodorant perfumes can be made by the use of materials from certain specified categories of perfume materials which makes it possible to obtain fragrances containing lower quantities of high boiling components while also obtaining good long term deodorant properties. Forms of this invention can deliver a deodorant performance which improves on that obtained from compositions exemplified in the prior documents above. In particular compositions according to the invention are good at reducing sulphurous malodours in body odour.

Accordingly, the present invention provides a perfume composition comprising (1) at least 15% by weight of the perfume composition of one or more aldehydes of general formula:

$R^1CHO$ having an octanol-water partition coefficient within the range of 2.0 to 4.4 (in logarithmic form), and wherein the group $R^1$ is a hydrocarbyl radical which may comprise aromatic or aliphatic groups, and mixtures thereof, and which may be cyclic or acyclic, straight chained or branched, and optionally substituted with other groups, with the proviso that at least 1% by weight of the perfume composition comprises aliphatic aldehydes of this general formula, and (2) at least 30%, preferably at least 70%, by weight of the perfume composition of at least one, preferably at least two, and more preferably at least three of the following five categories of perfumery ingredients;

a) at least 2.0%, preferably at least 4.0%, by weight of the perfume composition of one or more hydroxylic materials of general formula:

$R^1OH$ having an octanol-water partition coefficient within the range of 2.5 to 3.6 (in logarithmic form), and wherein the group $R^1$ is a hydrocarbyl radical containing no more than one olefinic double bond, and comprising aromatic or aliphatic groups, and mixtures thereof, and which may be cyclic or acyclic, straight chained or branched, and optionally substituted with other groups, b) at least 2.0%, preferably at least 4.0%, by weight of the perfume composition of one or more ketones of general formula:

$R^1COR^2$ having an octanol-water partition coefficient within the range of 3.0 to 4.1 (in logarithmic form), and wherein the groups $R^1$ and $R^2$ are independently hydrocarbyl radicals which may comprise aromatic or aliphatic groups, and mixtures thereof, and may be cyclic or acyclic, straight chained or branched, and optionally substituted with other groups, c) at least 2.0%, preferably at least 4.0%, by weight of the perfume composition of one or more ethers of general formula:

$R^1O R^2$ having an octanol-water partition coefficient within the range 3.0 to 4.0 (in logarithmic form), and wherein the groups $R^1$ and $R^2$ are independently hydrocarbyl radicals which may comprise aliphatic or aromatic groups, and mixtures thereof, and which may be straight chained or branched and optionally substituted with other groups, with the proviso that at least one of $R^1$ and $R^2$ comprises an olefinic double bond, d) at least 2.0%, preferably at least 4.0%, by weight of the perfume composition of one or more esters of general formula:

$R^1CO_2R^2$ having an octanol-water partition coefficient within the range 2.6 to 4.3 (in logarithmic form), and wherein the groups $R^1$ and $R^2$ are independently hydrocarbyl radicals which may comprise saturated aliphatic or aromatic groups, and mixtures thereof, and which may be straight chained or branched, cyclic or acyclic, and optionally substituted with other groups, and e) at least 2.0%, preferably at least 4.0% by weight of the perfume composition of one or more nitriles of general formula:

$R^1CN$ having an octanol-water partition coefficient within the range 3.0 to 4.4 (in logarithmic form), and wherein the group $R^1$ is a hydrocarbyl radical comprising an olefinic double bond, which may comprise aliphatic or aromatic groups, and mixtures thereof, and which may be straight chained or branched, cyclic or acyclic and optionally substituted with other groups.

The invention also provides a deodorant product comprising a perfume composition as defined above.

The invention further provides the use, as a deodorant, of a perfume composition and a deodorant product as defined above.

The term 'perfume material (or ingredient)' is herein taken to represent materials which may be acceptably employed within fragrances to provide an odour contribution to the overall hedonic performance of the fragrance.

Typically, such materials will be generally recognised as possessing odours in their own right, and will be relatively volatile, and characterised by molecular weights within the range of around 100 to 300 amu.

The concentration of perfume materials or ingredients referred to herein is relative to the total concentration of perfume components present in the composition, ie excludes, for example, the presence of any optional diluent.

The octanol-water partition coefficient (or its common logarithm to base 10, 'logP') is well known in the literature as an indicator of hydrophobicity and water solubility (see Hansch and Leo, *Chemical Reviews*, 526 to 616, (1971), 71; Hansch, Quinlan and Lawrence, *J.Organic Chemistry*, 347 to 350 (1968), 33). Where such values are not available in the literature they may be measured directly, or approximately estimated using mathematical algorithms. Software providing such estimations are available commercially, for example 'LogP' from Advanced Chemistry Design Inc. (ACD). For the purposes of the present invention the results obtained using ACD software are preferred.

A perfume composition according to the present invention has the following preferred features, either singly or in any combination;
  (i) hydroxylic materials of category (2)(a) which are one or more of
    Citronellol
    Dimethylheptanol
    Tetraihydrolinalol,
  (ii) aldehydes of category (1) which comprise less than two hydrogen atoms in the position directly adjacent to the formyl functional group,
  (iii) ethers of category (2) (c) in which $R^1$ comprises an alicyclic or aromatic ring, and
  (iv) esters of category (2)(d) in which $R^1$ or $R^2$ comprises an alicyclic or aromatic ring.

In cyclic esters according to category (2)(d), $R^1$ and $R^2$ may be directly connected, as in lactones.

In certain instances, it may be that materials are capable of classification into more than one category, for example, 4-(4'-hydroxy-4'-methylpentyl)cyclohex-3-enecarbaldehyde comprises both hydroxyl and formyl functional groups and hence could be a member of category (1) as well as (2)(a). In such cases the material is deemed to be within the first named category, that is, in (1) before (2), in (2)(a) before (2)(b) and so forth. Acetals are considered herein as ethers. With regard to the essential oils, synthetic oils and complex mixtures common within the perfumery business, the above rules must be applied to their individual constituents.

Preferred perfumes comprise at least 50%, more preferably at least 60%, and particularly at least 75% by weight of perfume ingredients as described herein. The perfume composition preferably comprises at least 2, more preferably at least 3, and particularly at least 4 of the 5 classes of perfumery ingredients (2)(a) to (2)(e).

The invention is directed to perfume compositions and to consumer products which provide a deodorant action when applied to the body within a cosmetically acceptable vehicle. Suitable deodorant products include, but are not limited to, deodorants and antiperspirants including different physical forms such as roll ons, gels, sticks, and aerosols, other personal products such as deocolognes, talcum powders, hand creams, lotions, skin and hair conditioners, sunscreens, soaps, shampoos, and shower gels.

The perfumes described herein may also be usefully employed for deodorant properties in other product areas, for example in detergent and household products such as laundry powders, laundry liquids, rinse conditioners, and household cleaning compositions. Perfumes of the inventions may also be incorporated into textiles directly during manufacture using techniques known in the art, to provide long lasting deodorant protection. It is also known in the art to carry or encapsulate perfumes within other materials such as porous solids or polymeric matrices, in order to provide extended lifetimes, and to provide the possibility of triggered release, for example, during perspiration. Such techniques are applicable within the scope of the present invention.

The invention is illustrate by the following examples.

EXAMPLES

Table 1 below presents a representative list of perfume materials falling within the above categories, together with comparative examples of commonly used perfume ingredients which do not fall within the categories.

Tables 2 to 4 illustrate the use of perfumes of the invention within deodorant products. Their preparation is well known to those skilled in the art.

A Sulphur Reduction Test, suitable for determining reduction of sulphurous malodours in body odour is as follows:

Take 200 $\mu$l of saturated vapour from above a vial containing equal weights of ethanetiol and methyl sulphide using a gas-tight syringe. Inject the sulphur-containing materials into the headspace volume of a closed glass vial containing 0.25 g of perfume of perfume ingredient. Allow to equilibrate for 2 minutes, then remove a small aliquot (e.g. 0.5 ml from a 20 ml vial) of mixed vapours from the headspace above the perfume material and analyse by gas chromatography. Care is taken throughout to preserve the integrity of both samples and reduce losses or contamination. The perfume/thiol/sulphide mixture is allowed to equilibrate for a further 13 minutes, after which a second aliquot is sampled and analysed as previously. The concentration of sulphurous materials in the vial headspace at 2 minutes and 15 minutes is compared. If the concentration has been reduced by 75% or more, the perfume or perfume ingredient is deemed useful for reducing sulphurous compounds.

TABLE 1

Examples of Ingredient Categorisation

| Material | Category |
|---|---|
| 1,3,4.6,7,8-hexahydro-4,6,6,7,8,8-hexamethylcyclopenta[g]-2-benzopyran | ex |
| 1-(3,5,5,6,8,8-hexamethyl-5,6,7,8-tetrahydro-2-naphthalenyl)-1-ethanone | ex |
| 1-Methyl-2-propenyl-4-isopropyl benzene | ex |
| 2-tert-Butylcyclohexyl acetate | (2) (d) |
| 2,4-dimethylcyclohex-3-ene-1-carbaldehyde | (1) |
| 2-Ethyl-4-(2,2,3-trimethyl-3-cyclopenten-1-yl)-2-buten-1-ol | ex |
| 2-methyl-3-(4'-(1"-methylethyl)phenyl)propanal | (1) |
| 4-(4'-hydroxy-4'-methylpentyl)cyclohex-3-enecarbaldehyde | (1) |
| 8,8-Dimethyl-7-(1-methylethyl)-6,10-dioxaspiro[4.5]decane | (2) (c) |
| Acetyl di-isoamylene | (2) (b) |
| Benzyl salicylate | ex |
| Cedrenyl acetate | ex |
| Citronellol | (2) (a) |
| Citronellyl nitrile | (2) (e) |
| Coumarin | ex |
| Diethyl phthalate | ex |
| Diethyldimethylcyclohex-2-en-1-one | (2) (b) |
| Dihydrojasmone | (2) (b) |
| Dihydrojasmone | (2) (b) |
| Dimethyl benzyl carbinyl acetate | (2) (d) |
| Dimethyl heptan-1-ol | (2) (a) |

TABLE 1-continued

Examples of Ingredient Categorisation

| Material | Category |
|---|---|
| Dipropylene glycol | ex |
| Florocylene | ex |
| Heliotropin | ex |
| Hexyl cinnamic aldehyde | ex |
| Hexyl salicylate | ex |
| Ionones | (2) (b) |
| Methyl ionones | ex |
| Methyl isoeugenol | (1) (c) |
| Phenylethyl alcohol | ex |
| Tetrahydrolinalol | (2) (a) |
| Undecalactone, gamma- | (2) (d) |
| Vanillin | ex |

Note: ex = excluded from classification

TABLE 2

Perfume composition

| Material | w/w % | category |
|---|---|---|
| 1,3,4,6,7,8-hexahydro-4,6,6,7,8,8-hexamethylcyclopenta[g]-2-benzopyran | 8.9 | |
| 2-tert-Butylcyclohexyl acetate | 2 | 2 (d) |
| 2,4-dimethylcyclohex-3-ene-1-carbaldehyde | 0.5 | 1 |
| 2,6,10-trimethylundec-9-enal | 0.2 | |
| 2-methyl-3-(4'-(1"-methylethyl)phenyl)propanal | 4.6 | 1 |
| 8,8-Dimethyl-7-(1-methylethyl)-6,10-dioxaspiro[4.5]decane | 6 | 2 (c) |
| Acetyl di-isoamylene | 5.5 | 2 (b) |
| Cassis base AB2967 (Q) | 0.6 | |
| Cervolide (Q) | 3 | |
| Diethyl phthalate | 9 | |
| Diethytdimethylcyclohex-2-en-1-one | 3 | 2 (b) |
| Dihydrojasmone | 0.5 | 2 (b) |
| Dimethyl benzyl carbinyl acetate | 2 | 2 (d) |
| Hexyl cinnamic aldehyde | 5.7 | |
| ionone, alpha- | 8.5 | 2 (b) |
| Methyl dihydrojasmonate | 12 | 2 (d) |
| Lyral ™ | 12 | 1 |
| Methyl isoeugenol | 2 | 2 (c) |
| Muguet base AB1951 (Q) | 2.5 | |
| Tetrahydrolinalol | 11 | 2 (a) |
| Undecalactone, gamma- | 0.5 | 2 (d) |
| total | 100% | |

1. Materials marked 'Q' are available from Quest International
2. Lyral is a mixture of 4-(4'-hydroxy-4'-methylpentyl)cyclohex-3-enecarbaldehyde and 3-(4'-hydroxy-4'-methylpentyl)cyclohex-3-enecarbaldehyde
3. The perfume comprises over 70% of ingredients according to the invention
5 The above perfume composition was particularly effective in the Sulphur Reduction Test.

TABLE 3

Deodorant stick

| Ingredient | Weight % |
|---|---|
| Ethanol | 44.0 |
| Sodium Stearate | 7.0 |
| Propylene glycol | 11.0 |
| Perfume | 1.0 |
| PEG-6-Caprylic/capric glycerides | 12.0 |
| Glycerin | 5.0 |
| Water | 20.0 |

TABLE 4

Deodorant aerosol

| Ingredient | Weight % |
|---|---|
| Isopropyl myristate | 3.0 |
| Propellants | to 100% |
| Fumed silica | 0.25 |
| Perfume | 1.5 |

TABLE 5

Roll-ons

| Ingredient | Weight % | Weight % |
|---|---|---|
| Ethanol | | 60.0 |
| Klucel MF | | 0.65 |
| Cremophor RM410 | | 0.5 |
| Bentone gel IPM (Rheox Inc.) | 27.0 | |
| Siliocone fluid DC344 (Dow Corning) | to 100% | |
| Aluminium chlorhydrate powder | 20.0 | |
| Perfume | 0.75 | 1.00 |
| Water | | to 100% |

What is claimed is:
1. A perfume composition comprising:
(1) at least 15% by weight of the perfume composition of one or more aldehydes of general formula:

$R^1CHO$ having an octanol-water partition coefficient within the range of 2.0 to 4.4 (in logarithmic form), and wherein the group $R^1$ is a hydrocarbyl radical which may comprise aromatic or aliphatic groups, and mixtures thereof, and which may be cyclic or acyclic, straight chained or branched, and optionally substituted with other groups, with the proviso that at least 1% by weight of the perfume composition comprises aliphatic aldehydes of this general formula, and
(2) at least 30% by weight of the perfume composition of at least two of the following five categories of perfumery ingredients;
a) at least 2.0% by weight of the perfume composition of one or more hydroxylic materials of general formula:

$R^1OH$ having an octanol-water partition coefficient within the range of 2.5 to 3.6 (in logarithmic form), and wherein the group $R^1$ is a hydrocarbyl radical containing no more than one olefinic double bond, and comprising aromatic or aliphatic groups, and mixtures thereof, and which may be cyclic or acyclic, straight chained or branched, and optionally substituted with other groups,
b) at least 2.0% by weight of the perfume composition of one or more ketones of general formula:

$R^1CO\ R^2$ having an octanol-water partition coefficient within the range of 3.0 to 4.1 (in logarithmic form), and wherein the groups $R^1$ and $R^2$ are independently hydrocarbyl radicals which may comprise aromatic or aliphatic groups, and mixtures thereof, and may be cyclic or acyclic, straight or branched, and optionally substituted with other groups, c) at least 2.0% by weight of the perfume composition of one or more ethers of general formula:

$R^1O\ R^2$ having an octanol-water partition coefficient within the range 3.0 to 4.0 (in logarithmic form), and wherein the groups $R^1$ and $R^2$ are independently hydrocarbyl radicals which may comprise aliphatic or aromatic groups, and mixtures thereof, and which may be straight or branched and optionally substituted with other groups, with the proviso that at least one of $R^1$ and $R^2$ comprises an olefinic double bond, d) at least 2.0% by weight of the perfume composition of one or more esters of general formula:

$R^1CO_2R^2$ having an octanol-water partition coefficient within the range 2.6 to 4.3 (in logarithmic form), and wherein the groups $R^1$ and $R^2$ are independently hydrocarbyl radicals which may comprise saturated aliphatic or aromatic groups, and mixtures thereof, and which may be straight chained or branched, cyclic or acyclic, and optionally substituted with other groups, and e) at least 2.0% by weight of the perfume composition of one or more nitriles of general formula:

$R^1CN$ having an octanol-water partition coefficient within the range 3.0 to 4.4 (in logarithmic form), and wherein the groups $R^1$ is a hydrocarbyl radical comprising an olefinic double bond, which may comprise aliphatic or aromatic groups, and mixtures thereof, and which may be straight chained or branched, cyclic or acyclic and optionally substituted with other groups, said perfume composition comprising 2-methyl-3-(4'-(1"-methylethyl)phenyl) propanal, acetyl di-isoamylene and 2-tert-butylcyclohexyl acetate as at least some of said aldehyde (1), ketone 2b) and ester 2d), respectively.

2. A perfume composition according to claim 1 wherein the hydroxylic materials of category (2) (a) comprise one or more of the following materials Citronellol Dimethylheptanol Tetrahydrolinalol.

3. A perfume composition according to either one of claim 1 or 2 wherein the aldehydes of category (1) comprise less than two hydrogen atoms attached to the carbon atom adjacent to the carbonyl function.

4. A perfume composition according to claim 1 wherein the ethers of category (c) comprise an alicyclic or aromatic ring within $R^1$.

5. A perfume composition according to claim 1 wherein the esters of category (d) comprise an alicyclic or aromatic ring within $R^1$ and $R^2$.

6. A perfume composition according to claim 1 comprising at least 50% by weight of perfume ingredients selected from (a)–(e).

7. A perfume composition according to claim 1 comprising at least 60% by weight of perfume ingredients selected from (a)–(e).

8. A perfume composition according to claim 1 comprising at least 75% by weight of perfume ingredients selected from (a)–(e).

9. A deodorant product comprising a perfume composition, as defined in claim 1.

10. A deodorant product according to claim 9 wherein the product is a personal product including shampoos, creams, lotions, conditioners, soaps and talcs.

11. A deodorant product according to claim 9 wherein the product is a laundry treatment product including detergents and rinse conditoners.

12. A method of deodorizing a surface which comprises applying to said surface, an effective amount of a perfume composition according to claim 1 or product according to claim 9.

13. A perfume composition according to claim 1 wherein (2) comprises at least 70% by weight of said composition of at least 2 or 3 of categories (a)–(e).

14. A perfume composition according to claim 13 wherein (2) comprises at least 4% by weight of the composition, of at least 2 or 3 of categories (a)–(e).

* * * * *